(12) United States Patent
Davis et al.

(10) Patent No.: US 6,336,919 B1
(45) Date of Patent: Jan. 8, 2002

(54) ABSORBENT PENIS SHIELD

(76) Inventors: Paul Davis; Cheryl Mitchell, both of 1101 Hawkins Dr., 9-H, Elizabethtown, KY (US) 42701

( * ) Notice: Subject to any disclaimer, the term of this patent is extended or adjusted under 35 U.S.C. 154(b) by 0 days.

(21) Appl. No.: 09/631,166

(22) Filed: Aug. 3, 2000

(51) Int. Cl.[7] ................................................. A61F 5/453
(52) U.S. Cl. ........................ 604/349; 604/346; 604/347; 604/352; 604/385.09
(58) Field of Search ................................ 604/346, 347, 604/352, 385.09

(56) References Cited

U.S. PATENT DOCUMENTS

| | | | | |
|---|---|---|---|---|
| 2,891,546 A | * | 6/1959 | Galloway | 128/295 |
| 4,576,599 A | * | 3/1986 | Lipner | 604/390 |
| 4,601,716 A | * | 7/1986 | Smith | 604/349 |
| 4,668,229 A | * | 5/1987 | Fago et al. | 604/327 |
| 4,790,835 A | * | 12/1988 | Elias | 604/349 |
| 4,886,509 A | * | 12/1989 | Mattsson | 604/349 |
| 5,643,235 A | | 7/1997 | Figuerido | 604/352 |
| 5,695,485 A | | 12/1997 | Duperret et al. | 604/349 |
| 5,735,837 A | * | 4/1998 | Ishikawa | 604/385.1 |
| 5,797,401 A | | 8/1998 | Knight | 128/842 |
| 5,827,250 A | | 10/1998 | Fujioka et al. | 604/349 |
| 5,827,257 A | | 10/1998 | Fujioka et al. | 604/385.1 |
| 6,105,174 A | * | 8/2000 | Nygren et al. | 2/403 |
| 6,209,142 B1 | * | 4/2001 | Mattsson | 2/403 |

* cited by examiner

Primary Examiner—John G. Weiss
Assistant Examiner—Michael Bogart
(74) Attorney, Agent, or Firm—Joseph N. Breaux

(57) ABSTRACT

An incontinence product that is securable over the head of a user's penis to absorb urine emitted during an incontinence episode. The absorbent penis shield includes an absorbent member and a moisture proof section. The absorbent member includes an absorbent penis head receiving cup positioned in the center thereof between opposed two top and bottom absorbent sections and between opposed left and right absorbent sections. The moisture proof section has the entire absorbent member bonded to a penis facing side thereof; left and right fastener portions on the penis facing side on either side of the bottom absorbent section; and a center fastener section on an exterior facing side adjacent to the top absorbent section. The left and right fastener portions are each wrappable around a respective side of a penis to be secured within the absorbent penis shield and into connection with the center fastener section in a manner to form a constriction around a base section of a penis to hold a head portion of a user's penis within the absorbent penis head receiving cup.

1 Claim, 4 Drawing Sheets

ABSORBENT PENIS SHIELD

TECHNICAL FIELD

The present invention relates to products for men suffering from incontinence and more particularly to an absorbent penis shield that is securable over the head of a user's penis to absorb urine that may be emitted during an incontinence episode; the absorbent penis shield including an absorbent member and a moisture proof section; the absorbent member including an absorbent penis head receiving cup positioned in the center thereof between opposed two top and bottom absorbent sections and between opposed left and right absorbent sections; the moisture proof section having the entire absorbent member bonded to a penis facing side thereof and having left and right fastener portions on the penis facing side on either side of the bottom absorbent section and a center fastener section on an exterior facing side adjacent to the top absorbent section; the left and right fastener portions each being wrappable around a respective side of a penis to be secured within the absorbent penis shield and into connection with the center fastener section in a manner to form a constriction around a base section of a penis to hold a head portion of a user's penis within the absorbent penis head receiving cup.

BACKGROUND ART

Incontinent men often feel uncomfortable wearing a diaper or other incontinence appliance that surrounds the lower portion of the wearer's torso. It would be desirable for these individuals to have an incontinence product for absorbing urine emitted during an incontinence episode that could be secured over the head of the user's penis to absorb urine and which would take the place of a large diaper sized appliance.

GENERAL SUMMARY DISCUSSION OF THE INVENTION

It is thus an object of the invention to provide an absorbent penis shield that includes an absorbent member and a moisture proof section; the absorbent member including an absorbent penis head receiving cup positioned in the center thereof between opposed two top and bottom absorbent sections and between opposed left and right absorbent sections; the moisture proof section having the entire absorbent member bonded to a penis facing side thereof and having left and right fastener portions on the penis facing side on either side of the bottom absorbent section and a center fastener section on an exterior facing side adjacent to the top absorbent section; the left and right fastener portions each being wrappable around a respective side of a penis to be secured within the absorbent penis shield and into connection with the center fastener section in a manner to form a constriction around a base section of a penis to hold a head portion of a user's penis within the absorbent penis head receiving cup.

Accordingly, an absorbent penis shield is provided. The absorbent penis shield includes an absorbent member and a moisture proof section; the absorbent member including an absorbent penis head receiving cup positioned in the center thereof between opposed two top and bottom absorbent sections and between opposed left and right absorbent sections; the moisture proof section having the entire absorbent member bonded to a penis facing side thereof and having left and right fastener portions on the penis facing side on either side of the bottom absorbent section and a center fastener section on an exterior facing side adjacent to the top absorbent section; the left and right fastener portions each being wrappable around a respective side of a penis to be secured within the absorbent penis shield and into connection with the center fastener section in a manner to form a constriction around a base section of a penis to hold a head portion of a user's penis within the absorbent penis head receiving cup.

BRIEF DESCRIPTION OF DRAWINGS

For a further understanding of the nature and objects of the present invention, reference should be made to the following detailed description, taken in conjunction with the accompanying drawings, in which like elements are given the same or analogous reference numbers and wherein.

EXEMPLARY MODE FOR CARRYING OUT THE INVENTION

Figure 1:
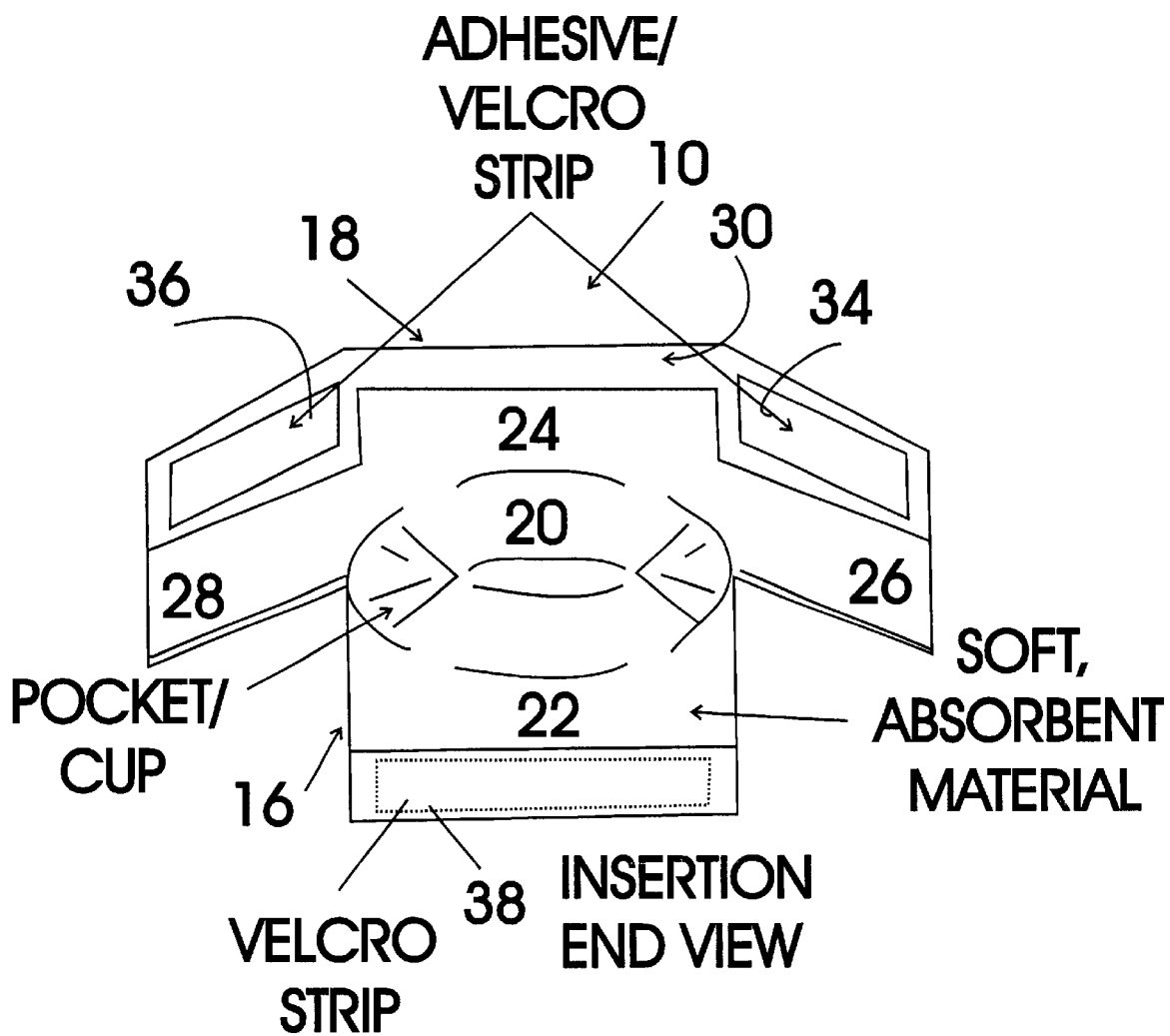
FIG. 1 is an interior end view of an exemplary embodiment of the absorbent penis shield of the present invention showing the absorbent member including the absorbent penis head receiving cup positioned in the center thereof between two top and bottom absorbent sections and between left and right absorbent sections, and a moisture proof section having the entire absorbent member bonded to a penis facing side thereof and having left and right fastener portions on the penis facing side on either side of the bottom absorbent section and a center fastener section on an exterior facing side adjacent to the top absorbent section; the left and right fastener portions each being wrappable around a respective side of a penis and into connection with the center fastener section in a manner to hold the head of a user's penis within the absorbent penis head receiving cup.
Figure 2:
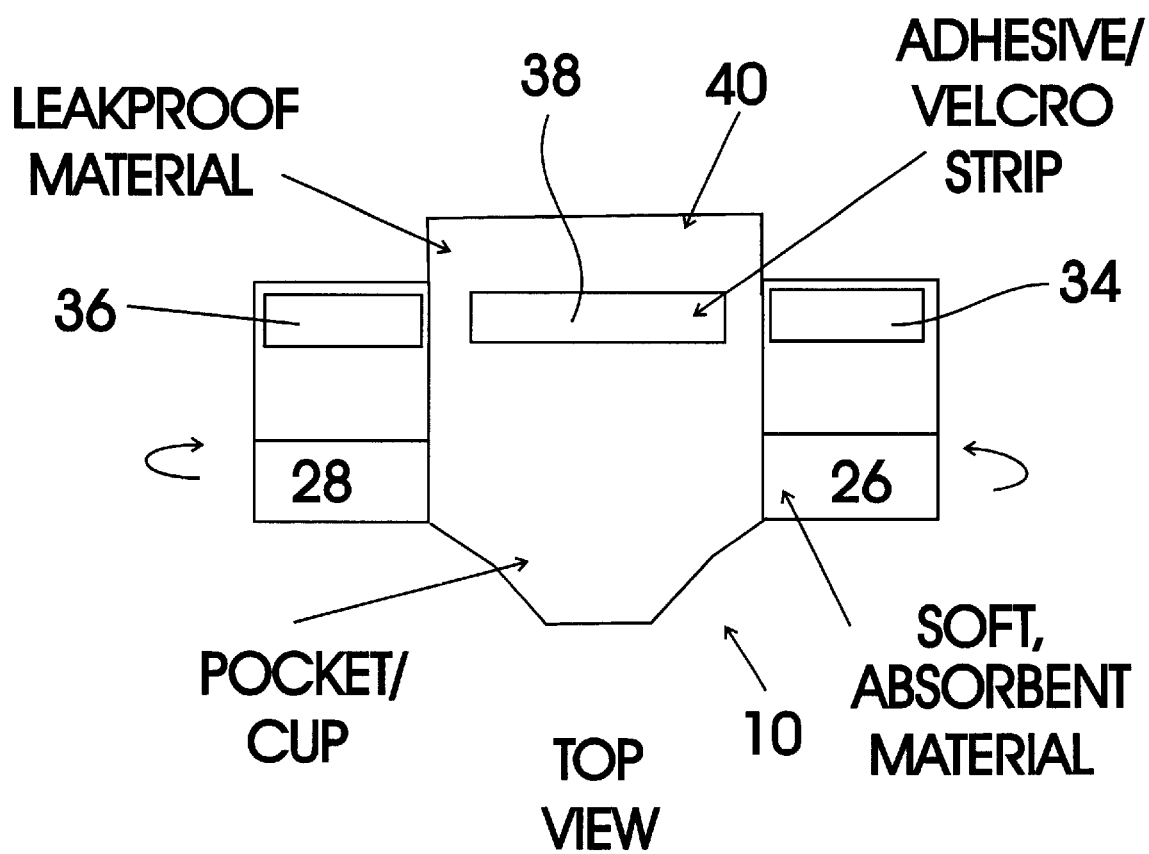
FIG. 2 is a top view of the exemplary absorbent penis shield of FIG. 1.
Figure 3:
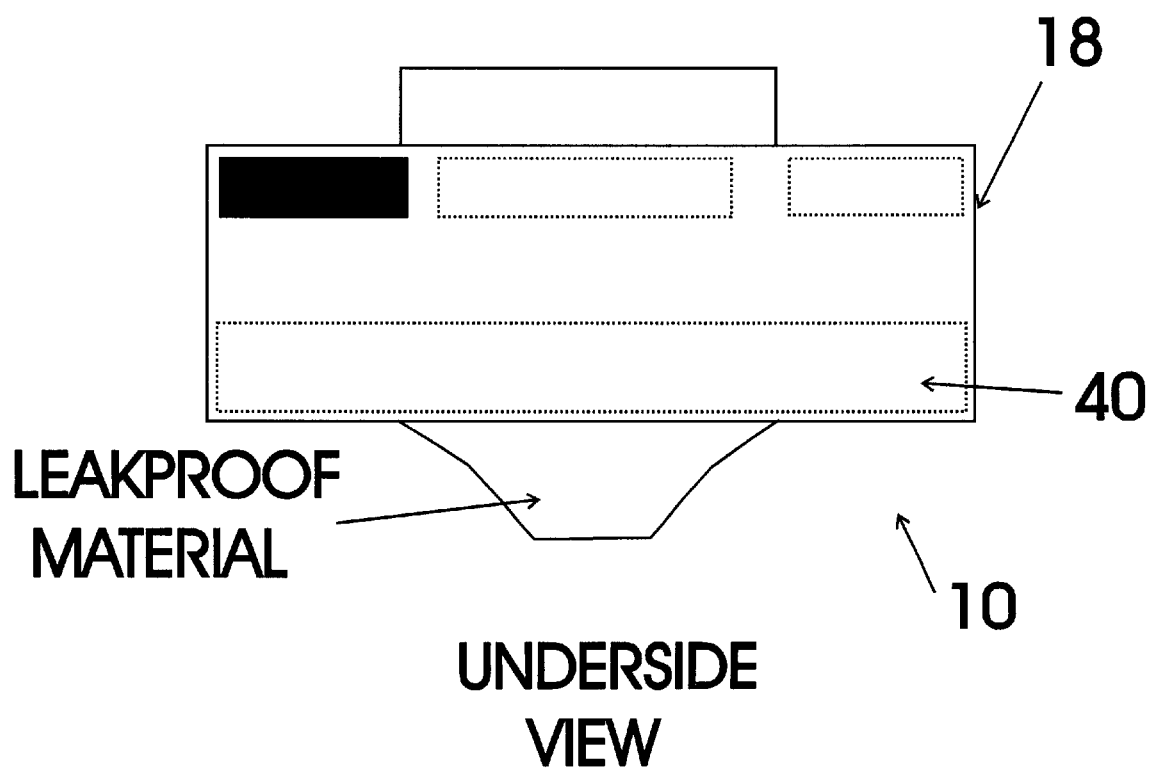
FIG. 3 is an underside view of the exemplary absorbent penis shield of FIG. 1.
Figure 4:
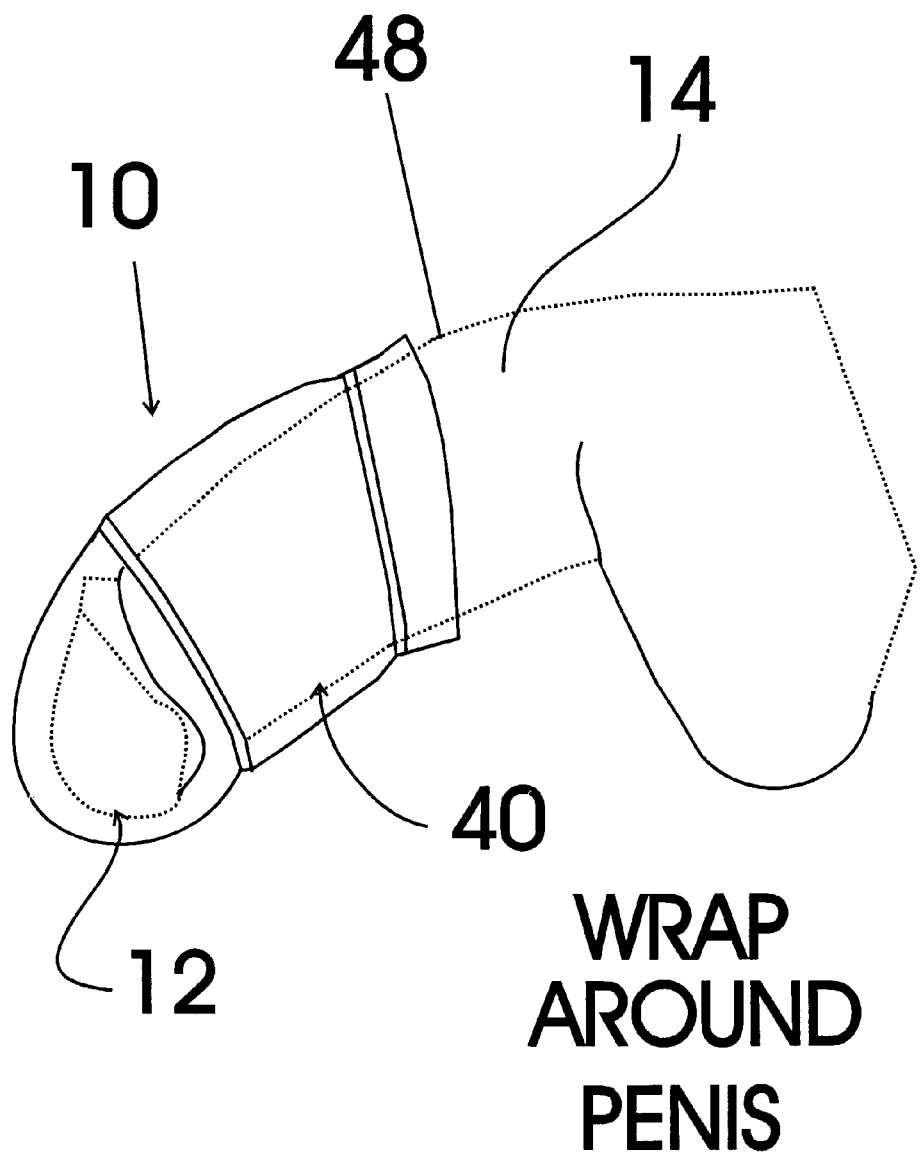
FIG. 4 is a side view of the exemplary absorbent penis shield of FIG. 1 in use on a representative penis, the penis being shown in dashed lines.

FIGS. 1–4 show various aspects of an exemplary embodiment of the absorbent penis shield of the present invention generally designated 10. In use absorbent penis shield 10 is securable over the head, generally designated 12 (shown in dashed lines in FIG. 4) of a user's penis 14 to absorb urine emitted during an incontinence episode.

Absorbent penis shield 10 includes an absorbent member, generally designated 16, and a moisture proof section, generally designated 18. Absorbent member 16 includes an absorbent penis head receiving cup 20 positioned in a center thereof between opposed top and bottom absorbent sections 22,24 and between opposed left and right absorbent sections 26,28. In this embodiment absorbent member 16 is constructed from an absorbent fiber material.

Moisture proof section 18 is a section of moisture proof plastic sheeting having the entire absorbent member 16 bonded to a penis facing side 30 thereof. Moisture proof section 18 has left and right fastener portions 34,36 on penis facing side 30 on either side of bottom absorbent section 24 and a center fastener section 38 on an exterior facing side 40 adjacent to top absorbent section 22. Left and right fastener portions 26,28 are each wrappable around a respective side of penis 14 to be secured within the absorbent penis shield 10 and into connection with the center fastener section 38 in a manner to form a constriction around a base section 48 of penis 14 to hold head portion 12 of user's penis 14 within absorbent penis head receiving cup 20. In use, urine emitted is absorbed by absorbent member 16. Moisture proof section 18 prevents moisture from migrating through absorbent member 16 an wetting the clothing of the user.

It can be seen from the preceding description that an absorbent penis shield has been provided.

It is noted that the embodiment of the absorbent penis shield described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. An absorbent penis shield that is securable over a head of a user's penis to absorb urine emitted during an incontinence episode; said absorbent penis shield comprising:

an absorbent member; and a moisture proof section;

said absorbent member including an absorbent penis head receiving cup positioned in a center thereof between opposed two top and bottom absorbent sections and between opposed left and right absorbent sections;

said moisture proof section having said entire absorbent member bonded to a penis facing side thereof and having left and right fastener portions on said penis facing side on either side of said bottom absorbent section and a center fastener section on an exterior facing side adjacent to said top absorbent section;

said left and right fastener portions each being wrappable around a respective side of a penis to be secured within said absorbent penis shield and into connection with said center fastener section in a manner to form a constriction around a base section of a penis to hold a head portion of a user's penis within said absorbent penis head receiving cup.

* * * * *